(12) United States Patent
Kuzum et al.

(10) Patent No.: US 11,224,372 B2
(45) Date of Patent: Jan. 18, 2022

(54) GRAPHENE-PASSIVATED IMPLANTABLE ELECTRODES

(71) Applicant: THE TRUSTEES OF THE UNIVERSITY OF PENNSYLVANIA, Philadelphia, PA (US)

(72) Inventors: Duygu Kuzum, Ardmore, PA (US); Ertugrul Cubukcu, Ardmore, PA (US); Brian Litt, Bala Cynwyd, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 167 days.

(21) Appl. No.: 15/110,216

(22) PCT Filed: Jan. 6, 2015

(86) PCT No.: PCT/US2015/010224
§ 371 (c)(1),
(2) Date: Jul. 7, 2016

(87) PCT Pub. No.: WO2015/105759
PCT Pub. Date: Jul. 16, 2015

(65) Prior Publication Data
US 2016/0324435 A1 Nov. 10, 2016

Related U.S. Application Data

(60) Provisional application No. 61/924,315, filed on Jan. 7, 2014.

(51) Int. Cl.
*A61B 5/291* (2021.01)
*A61B 5/24* (2021.01)
*A61N 1/05* (2006.01)

(52) U.S. Cl.
CPC ............ *A61B 5/291* (2021.01); *A61B 5/24* (2021.01); *A61N 1/0534* (2013.01); *A61N 1/0551* (2013.01); *A61B 2562/125* (2013.01)

(58) Field of Classification Search
CPC .... A61N 1/00; A61B 5/04001; A61B 5/0478; A61B 5/6868; A61B 5/6846; A61B 5/484;
(Continued)

(56) References Cited

U.S. PATENT DOCUMENTS

| 8,455,927 B2 | 6/2013 | Fife |
| 2010/0203340 A1* | 8/2010 | Ruoff .................. C23C 28/345 428/408 |

(Continued)

FOREIGN PATENT DOCUMENTS

| WO | 2011159923 A2 | 12/2011 |
| WO | 2012075120 A2 | 6/2012 |

OTHER PUBLICATIONS

International Preliminary Report on Patentability for International Application No. PCT/US2015/010224, dated Jul. 12, 2016, 7 pages.
(Continued)

*Primary Examiner* — Eun Hwa Kim
(74) *Attorney, Agent, or Firm* — BakerHostetler (57) ABSTRACT

An implantable electrode for use in the body of a subject has a metal layer and a graphene passivation layer formed on at least a portion of the metal layer. The graphene passivation layer may be a single monolayer of graphene. A process for passivating an implantable electrode is also disclosed.

8 Claims, 12 Drawing Sheets

(58) Field of Classification Search
CPC ............ A61B 5/4852; A61B 2562/043; A61B 2562/046; A61B 5/25; A61B 5/263; A61B 5/268
See application file for complete search history.

(56) References Cited

U.S. PATENT DOCUMENTS

| | | | | |
|---|---|---|---|---|
| 2010/0298895 | A1* | 11/2010 | Ghaffari | A61B 1/00082 607/3 |
| 2010/0323113 | A1* | 12/2010 | Ramappa | C23C 14/0605 427/398.1 |
| 2011/0230747 | A1* | 9/2011 | Rogers | A61B 5/05 600/377 |
| 2011/0309336 | A1 | 12/2011 | Shin et al. | |
| 2012/0080086 | A1 | 4/2012 | Yoon et al. | |
| 2012/0186998 | A1* | 7/2012 | Hermans | A61B 5/1486 205/780.5 |
| 2012/0241069 | A1* | 9/2012 | Hofmann | C01B 32/184 156/60 |
| 2013/0085359 | A1 | 4/2013 | Yao et al. | |
| 2013/0090542 | A1* | 4/2013 | Kipke | A61N 1/0551 600/377 |
| 2013/0338744 | A1* | 12/2013 | Frewin | A61N 1/0551 607/116 |
| 2015/0247041 | A1* | 9/2015 | Papakonstantinou | C23C 16/26 428/216 |
| 2015/0367124 | A1* | 12/2015 | Noda | A61N 1/0531 607/116 |
| 2016/0100768 | A1* | 4/2016 | Someya | A61B 5/0478 600/393 |

OTHER PUBLICATIONS

International Search Report and Written Opinion for PCT/US2015/010224, dated Apr. 29, 2015, pp. 1-10.

* cited by examiner

GRAPHENE-PASSIVATED IMPLANTABLE ELECTRODES

CROSS REFERENCE TO RELATED APPLICATIONS

This application is the U.S. National Phase application of PCT International Application PCT/US2015/010224, filed on Jan. 6, 2015, which claims the benefit of U.S. Provisional Application No. 61/924,315, titled "GRAPHENE-PASSIVATED IMPLANTABLE ELECTRODES", filed on Jan. 7, 2014, the entirety of which are incorporated by reference herein and for all purposes.

FIELD OF THE INVENTION

The present invention relates to electrodes for implanting in the body of a subject. More specifically, the invention relates to metal electrodes passivated by graphene.

BACKGROUND OF THE INVENTION

Implantable devices for use in the body of a subject, such as neural prosthetic systems, have had limited success due to the challenges presented by the environment the devices are exposed to. Long-term interaction with the implantable device and the body takes a toll on these implantable devices. Impedance degradation, scar tissue formation, and inflammation around the implant area can have deleterious effects on the functioning of implanted devices. Building robust and scalable long-term implants could advance the understanding of brain networks related to network disorders, including epilepsy, schizophrenia, depression, and movement disorders, and could lead to targeted treatments through prosthetic devices. Therefore, it is desirable to develop long-lasting, high performance implantable devices.

The body presents a difficult environment for electrical devices. Chemical reactions can degrade implanted devices over time, rendering the devices ineffective or unusable. The materials used in the implanted devices must be carefully selected based on biocompatibility and their ability to perform their desired role in the body of a subject. Often, materials having the most desirable properties for the functioning of the device are chemically reactive or toxic when inserted in the body.

Electrical devices implanted within the body have an additional set of hurdles to overcome as they must be small enough to fit in the body while preserving the desired electrical functions. Many materials used in electrical devices are chemically reactive or toxic. Such materials must either be avoided or shielded so that they do not contact the body. Other materials have a tendency to break down over time, which may trigger an immune response if the device is not removed or replaced. The main issues degrading long-term stability of implantable electrodes are the tissue damage and inflammatory scar tissue response, the corrosion of electrodes, and the impedance change over time.

Electrodes for use in the body of a subject, such as an animal or human, must satisfy several requirements. The electrode must be small enough to be implanted, the electrode must be bio-compatible, non-corrosive, and durable, and the electrode must be highly conductive to be able to transmit an electrical signal.

Conventional electrodes comprise a metal conductor either composed of or covered with an inert material, such as, for example, platinum, iridium or gold, to form a passivation layer. Due to the use of such materials, conventional electrodes can be expensive. Conventional implantable electrodes are limited due to their impedance and noise characteristics, as well as their signal-reproducing characteristics.

The narrow selection of usable inert materials also limits the electrical properties of the electrodes. Oftentimes, a conductor comprised of a metal having more ideal electrical properties is covered with a material having a greater biocompatibility that has less satisfactory electrical properties, which may lead to lower signal-to-noise ratios.

Other known electrodes sacrifice electrical performance for bio-compatibility. For example, some materials that have ideal electrical properties (e.g., low noise, impedance, and ability to be formed into small, thin electrodes) may be immunogenic, corrode, or toxic to tissues. Electrode materials that provoke less of an immune response may be undesirable in their electrical characteristics, such as how polarizable they are, how faithfully they reproduce electrical waveforms (e.g., how much they filter signals), and their impedance and noise characteristics.

One approach to designing neural electrodes is disclosed in WO 2012/075120. WO 2012/075120 discloses graphene electrodes formed on a silicon carbide substrate which are formed by subliming the silicon at the surface to create epitaxial graphene layers. The graphene layers are then fashioned into electrodes using lithography and etching techniques.

WO 2011/159923 discloses an implantable electrode comprising a core material having one or more non-conductive regions covered with a non-conductive biocompatible polymer. The core material of the electrode disclosed in WO 2011/159923 is preferably carbon and may comprise graphene. WO 2011/159923 also discloses that electrically conductive regions may include a conductive polymer, polypyrrole, platinum, platinum black, iridium oxide, graphene, and carbon nanotubes.

U.S. Patent Application Publication No. 2013/0085359 discloses a process for forming flexible microelectrodes comprising growing a graphene electrode layer on a temporary substrate, growing a flexible substrate on the graphene electrode layer, and removing the temporary substrate to form an electrode body comprising the graphene electrode layer and the flexible substrate. The flexible substrate is made of an electrically insulating material.

There is a need for implantable electrodes that have long-term stability, high conductivity, scalability, and biocompatibility. The present invention provides an implantable electrode having at least one of these features.

SUMMARY OF THE INVENTION

One aspect of the present invention relates to an electrode for use in the body of a subject comprising a metal conductor and a graphene passivation layer covering at least a portion of the metal conductor, wherein the graphene passivation layer comprises a monolayer of graphene.

Another aspect of the present invention relates to a neural electrode comprising a bi-component conductor, wherein the bi-component conductor consists of a metal layer and a graphene layer, wherein the graphene layer covers at least a portion of the metal layer.

Yet another aspect of the present invention relates to a process for forming an electrode for use in the body of a subject, comprising coating a metal layer with a graphene passivation layer, wherein the graphene passivation layer covers at least a portion of the metal layer.

DETAILED DESCRIPTION OF THE INVENTION

One aspect of the present invention relates to a metal implantable electrode including a graphene passivation layer.

As used herein, the term "electrode" refers to a transducer that connects the body to a device for sending or receiving electrical signals. The electrode may transmit an electrical signal to the body (e.g., provide a stimulation), transmit an electrical signal from the body (e.g., sense or monitor activity), or both. As used herein, the term "electrode" may be used interchangeably with "probe" or "sensor." The electrodes may be neural electrodes, pacemaker electrodes, deep brain stimulation (DBS electrodes), BMI (brain-machine interface) electrodes, intracranial EEG electrodes, penetrating intracortical electrode arrays, such as Utah-type arrays or Michigan-type arrays, or other implantable electrodes connected to treatment or measurement devices. The electrodes may be used for electrophysiological research and clinical functional treatments, including deep brain stimulation (e.g., Parkinson's disease, essential tremor, obsessive compulsive disorder, dystonia, and epilepsy), and stimulation of muscles and peripheral nerves (e.g., chronic pain, gastroparesis, bowel incontinence, overactive bladder, urinary retention, and severe spasticity).

According to at least one embodiment of the present disclosure, the electrode comprises a bi-component conductor comprising a metal layer and a graphene passivation layer.

In at least one embodiment, the metal is chosen from platinum, gold, iridium, tungsten, stainless steel, silver, copper, nickel, and alloys or combinations thereof. Other metals may also be used. As used herein, the term "alloy" refers to a homogeneous mixture of at least two different materials. The phrase "combinations thereof" refers to non-homogeneous mixtures of metals. For example, an electrode may comprise two metals with one metal coating another metal, such as, for example, an electrode comprising a silver layer formed over a copper layer. As used herein, the term "metal" also includes conductive metal-containing compounds, such as, for example, iridium oxide, silver chloride and tin nitride.

The metal electrode of the present disclosure comprises a graphene passivation layer. As used herein, the term "passivation layer" and variations thereof, refers to a layer that prevents corrosion and chemical reactions with the underlying layers and the surrounding environment. As a passivation layer, graphene may block chemical reactions between the underlying metal and body tissues. Therefore, the use of a graphene passivation layer may allow for the use of otherwise toxic materials in the electrode. Thus, by isolating the metal from the body, the graphene passivation layer allows for the use of any metal in the electrode, which may allow for the use of metals more efficient in charge transfer than the currently available metals used. The use of metals more efficient in charge transfer may increase battery life and lower the cost of current implantable devices.

The graphene passivation layer also prevents diffusion of gas molecules, i.e., the graphene passivation layer can function as a gas barrier layer. By blocking gases from the metal layer, the graphene can prevent corrosion of the metal, which may allow the electrodes to be implanted for longer times.

Graphene has a low impedance and high charge injection capacity that may allow scaling to single-cell levels. Graphene monolayers have a thickness of approximately 0.34 nm. Therefore, when a single graphene monolayer is used as a passivation layer, the passivation layer adds minimal thickness to the electrode. Due to its high electrical conductance, the graphene layer is expected to have minimal impact on the electrical properties of the underlying metal. Therefore, the electrical properties of the electrode are similar to the electrical properties of the underlying metal, which may allow for more faithful reproduction of electrical signals for improved sensing, stimulation, and other methods of interacting with biological tissues.

In at least one embodiment, the electrode comprises a single graphene monolayer as the passivation layer over the metal conductor.

According to at least one embodiment, the electrode may comprise a graphene layer comprising a thicker layer of graphene. For example, the electrode may comprise two or more monolayers of graphene.

In accordance with at least one embodiment, the graphene may be doped. Doping the graphene may further decrease the impedance of the graphene. For example, the graphene may be doped with nitric acid to form P-type doped graphene. Other dopants may also be used. In at least one embodiment, the graphene layer is doped by contacting the graphene with nitric acid.

In embodiments wherein the graphene passivation layer comprises a plurality of graphene monolayers, one or more of the graphene monolayers may be doped. In at least one embodiment, all of the graphene monolayers may be doped. When forming the graphene layers, the graphene may be doped between the formation of each graphene layer. For example, when the graphene layers are mechanically transferred, the graphene may be exposed to a dopant after each layer is transferred.

The implantable electrodes according to the present disclosure may have any form known in the art. For example, the implantable electrode may have the form of long, thin wires, short wire contacts connected to a microelectronic chip, flat contacts, shanks, needle-shaped electrodes, paddle- or spade-shaped electrodes, or electrodes that taper from wider to narrower.

Examples of implantable electrodes are shown in FIGS. 19-22.

Figure 19:
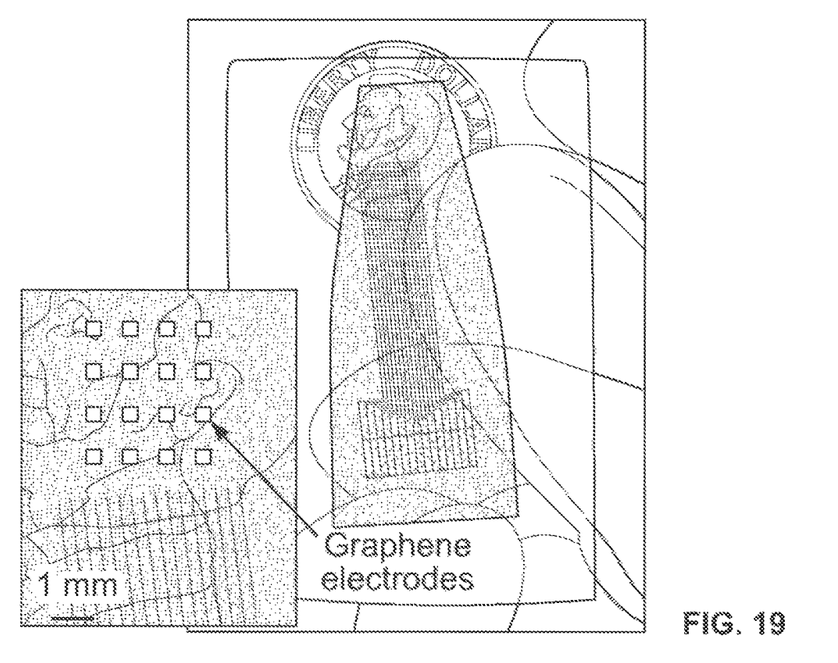
FIG. 19 shows a 16-electrode transparent array.

FIG. 19 shows a 16-electrode transparent array, with an enlarged portion showing the exposed contacts as square-shaped regions.

Figure 20:
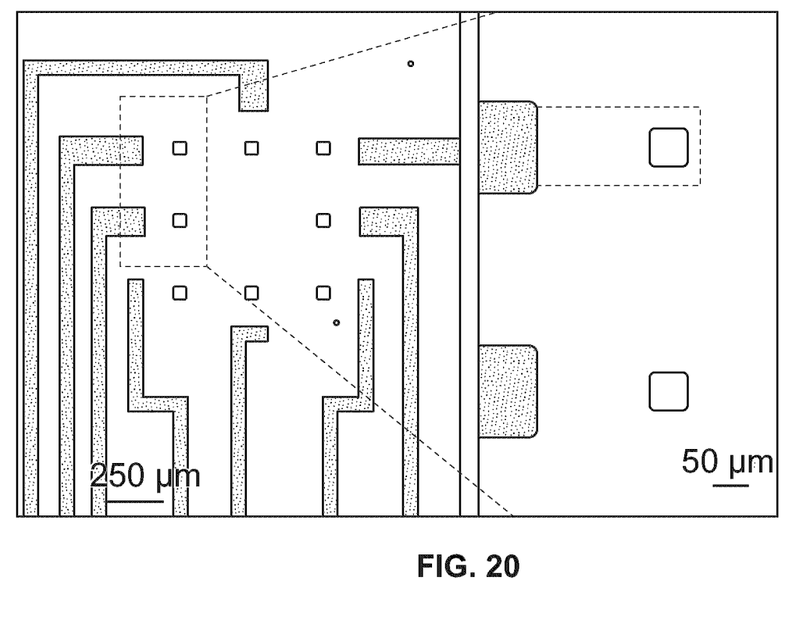
FIG. 20 shows an 8-electrode hippocampal slice array.

FIG. 20 shows an 8-electrode hippocampal slice array, with an enlarged portion showing the exposed contacts as square-shaped regions.

Figure 21:
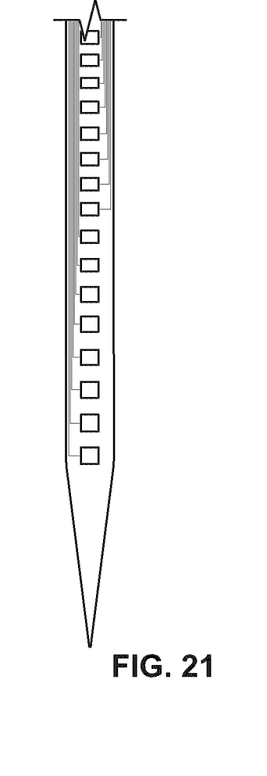
FIG. 21 shows an illustration of a minimally-invasive depth penetrating electrode array.

FIG. 21 shows a minimally-invasive depth penetrating electrode.

Figure 22:
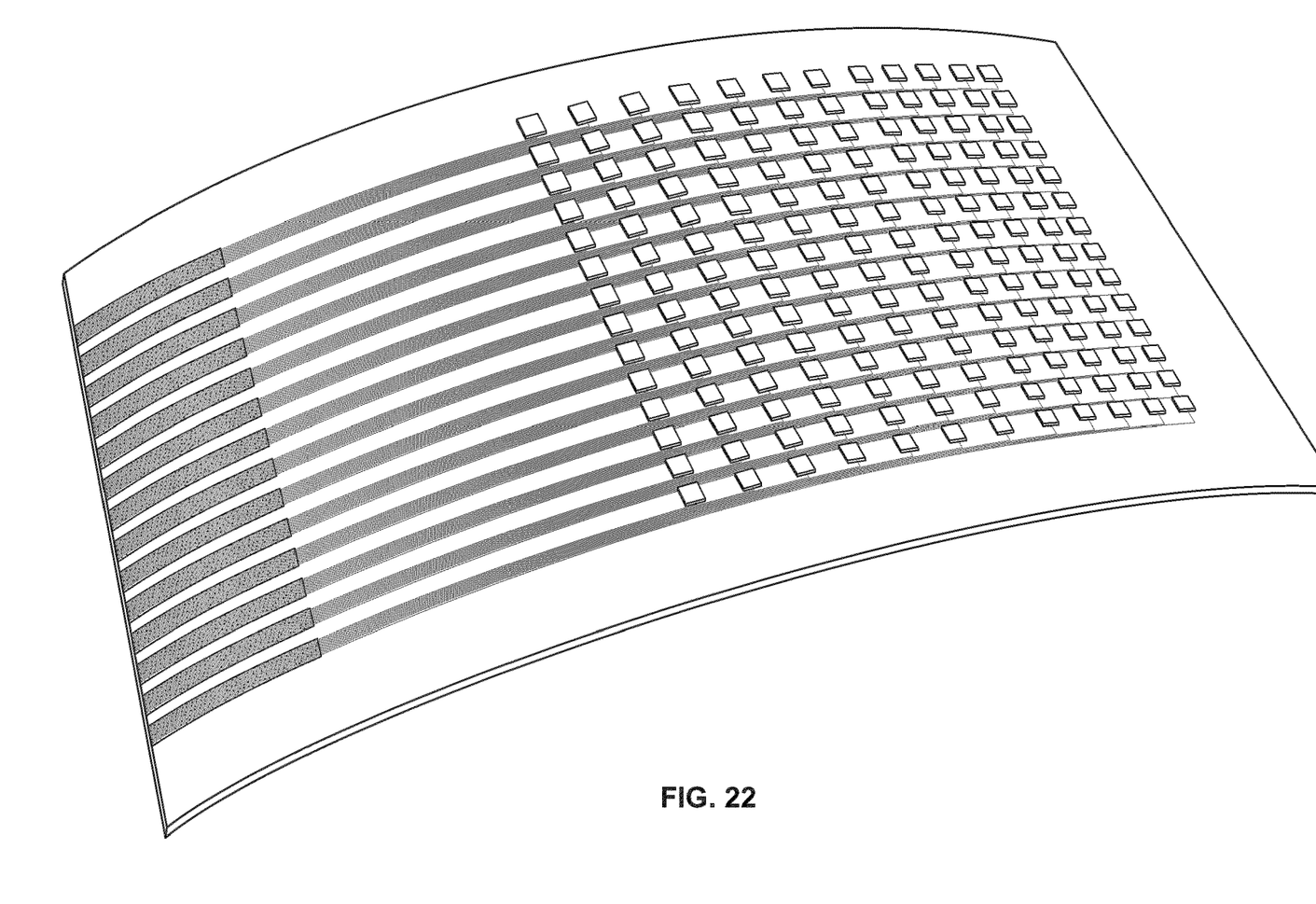
FIG. 22 shows an illustration of a large area, high-density surface array.

FIG. 22 shows a large area surface array.

The implantable electrodes according to the present disclosure may be incorporated into electrode arrays, such as, for example, in penetrating intracortical electrode arrays. The electrodes may be supported by a flexible or rigid substrate, integrated within electronic chips or semiconductor devices, or incorporated into cuffs, such as neural or tissue electrode cuffs and sheets.

In at least one embodiment, the electrode array is supported by a flexible substrate. When a flexible substrate is used, the electrode arrays may be flexible which may allow the electrode array to conform to curved or non-uniform surfaces.

According to at least one embodiment, the implantable electrodes comprise an electrically insulating coating. For example, the implantable electrode may comprise an electrically insulating coating covering all but a conductive contact on the electrode. In other embodiments, the electrically insulating coating may reveal more than one conductive contact on the electrode. The electrically insulating coating may comprise any material known in the art of implantable electrodes, such as, for example, bio-compatible, insulating polymers including poly(p-xylylene) polymers.

According to at least one embodiment, the implantable electrode comprises a conductive metal layer, an electrically insulating coating formed over the metal layer and defining at least one conductive contact on the metal layer, and a graphene passivation layer covering at least the conductive contact of the metal layer. The graphene passivation layer may cover the entire metal layer or may cover a portion of the metal layer including the at least one conductive contact. Preferably, the graphene passivation layer covers the entire metal layer.

In at least one embodiment, the graphene passivation layer may comprise a single graphene monolayer covering the entire metal layer. Additional graphene layers may be present at the at least one conductive contact.

Due to the transparency of graphene, the implantable electrodes according to the present disclosure may be transparent.

In at least one embodiment, the implantable electrode comprises bi-component conductor and an electrically insulating coating. The bi-component conductor comprises or consists of a metal core and a graphene passivation layer. The electrically insulating coating covers the bi-component conductor and defines at least one conductive contact which is not covered by the electrically insulating coating. The graphene passivation layer may cover all of the metal core or a portion of the metal core including the at least one conductive contact.

The graphene passivation layer may be formed by any known method. For example, the graphene passivation layer may be formed by chemical vapor deposition (CVD) directly onto the metal layer or the graphene passivation layer may be mechanically transferred.

In mechanical transfer methods, graphene may be formed in any known manner on a substrate, such as, for example, a copper or nickel substrate, and then transferred to a preformed electrode using a transfer layer. In this manner, graphite can be formed on a substrate that promotes proper graphite formation and then transferred to a metal layer that is not as conducive to graphite growth.

In accordance with at least one embodiment, graphene is grown on a copper substrate using a CVD process. A transfer layer comprising a layer of poly(methyl methacrylate) (PMMA) backed by poly(dimethyl siloxane) (PDMS) is used to remove the graphene layer from the copper substrate. After the copper is etched away, the graphite is transferred to the metal layer of the electrode and the transfer layer is peeled away. The transferred graphite layer can be subsequently patterned to achieve the desired electrode.

Masking techniques may be used to define areas in which the graphene passivation is formed. For example, a photoresist mask may be used to define the desired graphene pattern to etch the graphene to fit the underlying metal layer. Alternatively, when the graphene is formed directly on the metal layer of the electrode, a mask may be used to define the areas for graphene growth. Masking may also be used to apply an electrically insulating material and define conductive contacts on the electrode.

Various basic electrode geometries are shown in FIGS. 1-4. The electrodes of FIGS. 1-4 show different shapes and arrangements of the metal, graphene, and insulating layers, which are not drawn to scale. The electrodes of FIGS. 1-4 can be connected to an device, arranged within an array of electrodes, or attached to a substrate.

Figure 1:
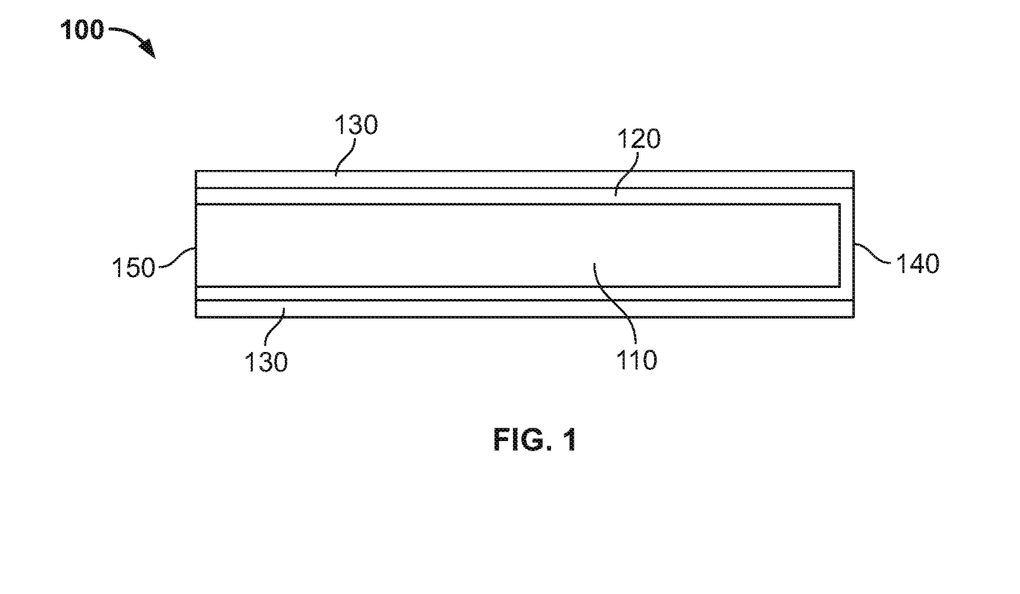
FIG. 1 is a schematic representation of an implantable electrode having a conductive contact at the end of the electrode.
Figure 6:
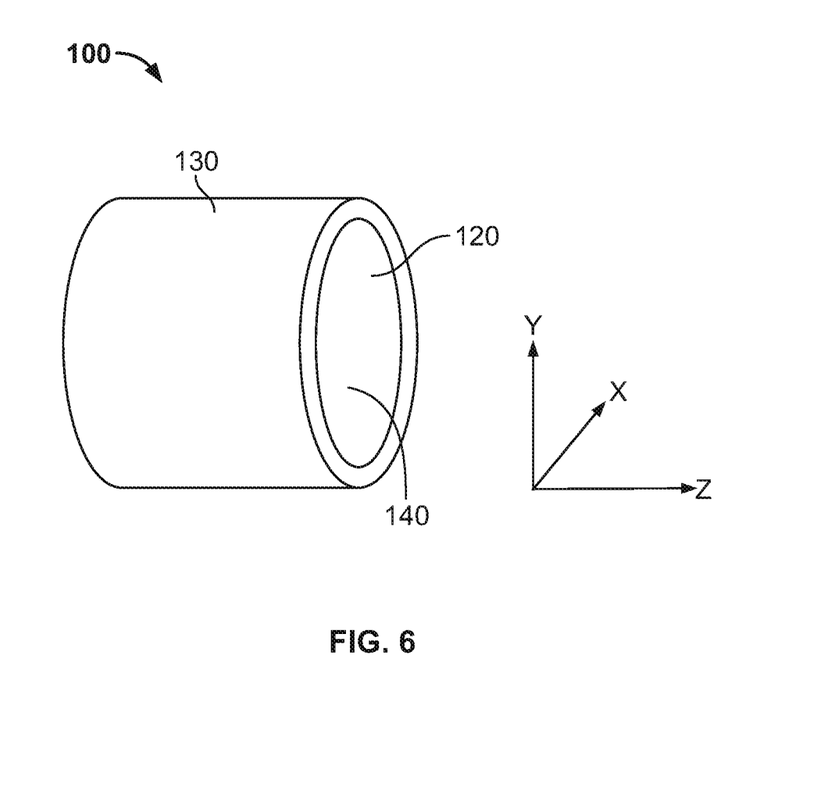
FIG. 6 is a perspective view of the electrode of FIG. 1.

FIG. 1 shows an electrode 100 according to an embodiment of the present disclosure. Electrode 100 comprises a metal core 110. A graphene passivation layer 120 is formed on the metal core 110 and covers the entire surface of the electrode 100. An electrically insulating coating 130 covers the electrode 100 except for the end, which forms a conductive contact 140. The opposing end 150 connects the electrode to a device such as a treatment or measurement device or to a substrate. A perspective view of the electrode 100 of FIG. 1 is shown in FIG. 6. As shown in FIG. 6, the electrode 100 has a circular cross-section. However, other geometries are also possible. For example, the electrode could have a square or rectangular cross-section, a flat cross-section in which the width (dimension in the x-axis) is significantly larger than the thickness (dimension in the y-axis), or other geometry.

Figure 2:
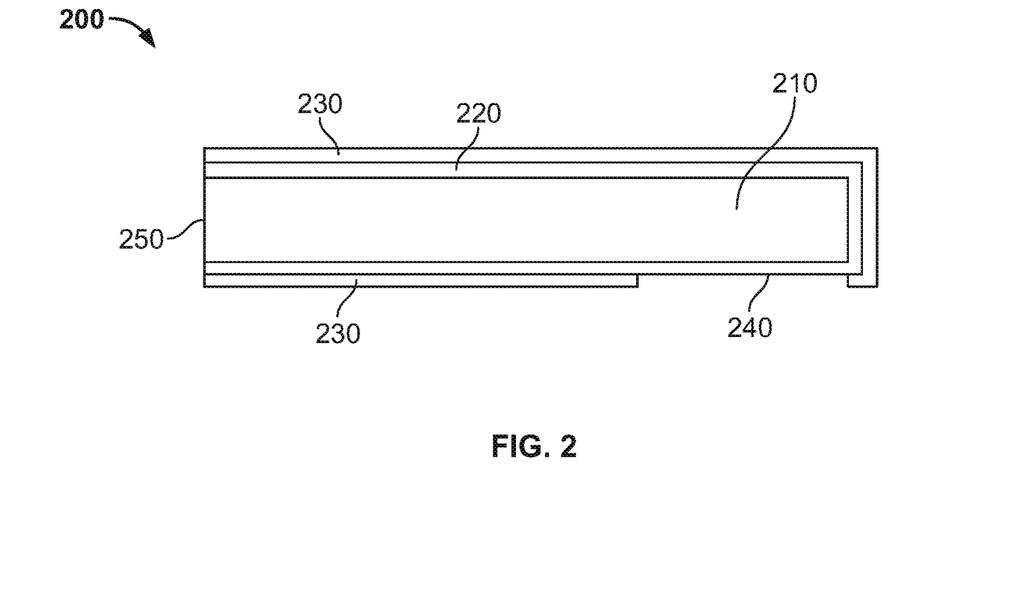
FIG. 2 is a schematic representation of an implantable electrode having a conductive contact on the side of the electrode.

FIG. 2 shows an electrode 200 having a different placement of the conductive contact compared to electrode 100 of FIG. 1. Electrode 200 comprises a metal core 210 and a graphene passivation layer 220 covered the entire surface of metal core 210. An electrically insulating coating 230 covers the passivation layer 220 except for the conductive contact 240. The end 250 of electrode 200 connects the electrode 200 to a device or substrate.

Figure 3:
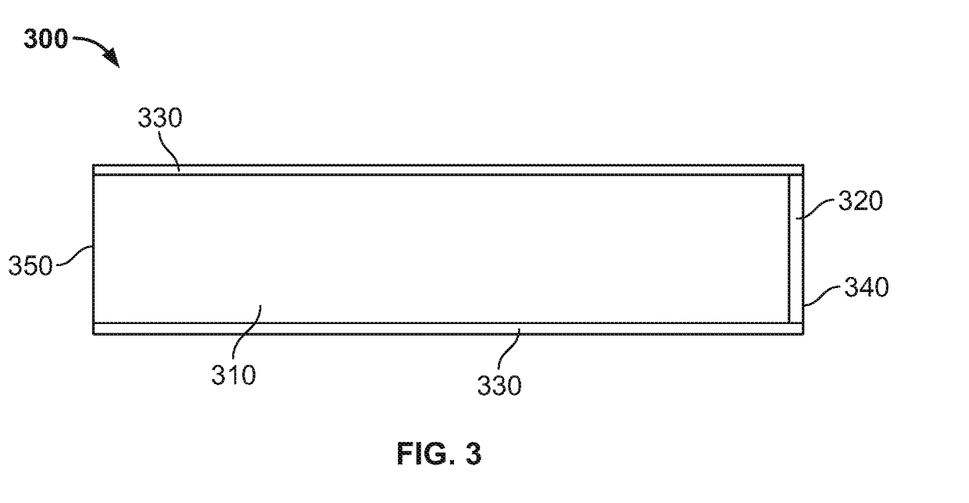
FIG. 3 is a schematic representation of an implantable electrode having a passivation layer formed on a portion of the metal conductive core.

In FIG. 3, electrode 300 has a graphene passivation layer 320 present only on the conductive contact 340. Electrode 300 comprises a metal core 310 having the passivation layer 320 disposed at one end of the electrode. An electrically insulating coating 330 covers the surface of metal core 310 not covered by the passivation layer 320. Electrically insulating coating 330 may overlap passivation layer 320 to ensure that the metal core 310 is not exposed. Electrode 300 may be connected to a device or substrate at end 350.

Figure 4:
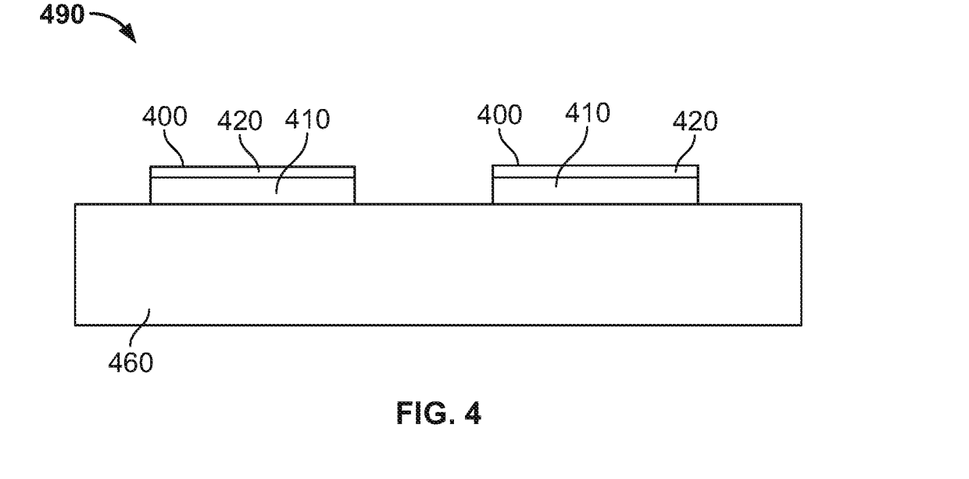
FIG. 4 is a schematic representation of an implantable electrode array formed on a substrate.

FIG. 4 shows an electrode array 490 comprising two electrodes 400 on a substrate 460. Each electrode 400 comprises a metal layer 410 and a graphene passivation layer 420 covering the top surface of metal layer 410. The electrodes 400 may be electrically connected to other features (not shown) on the substrate through wires or other conductors (not shown).

Figure 5:
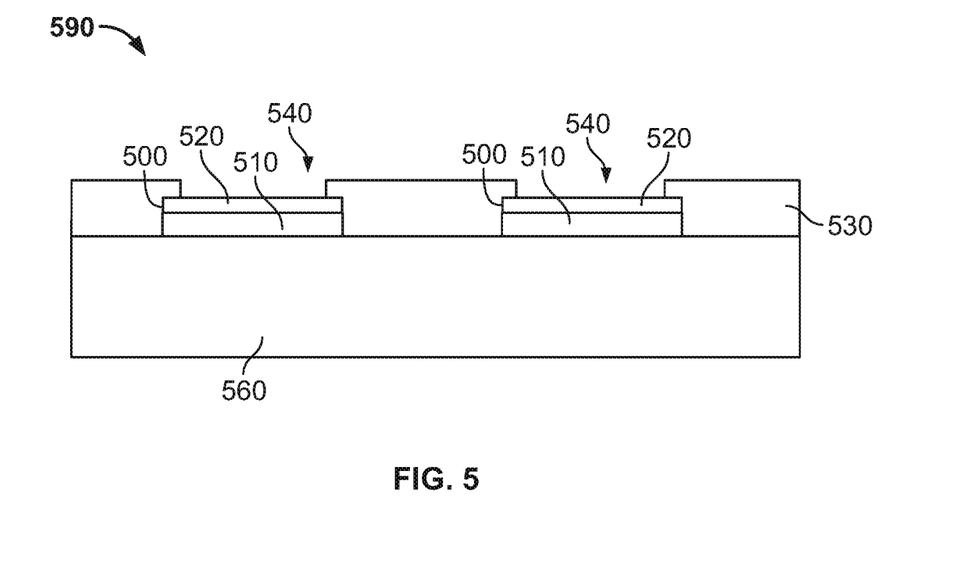
FIG. 5 is a schematic representation of an encapsulated electrode array.

FIG. 5 shows an electrode array 590 based on the basic electrode design shown in FIG. 4. In FIG. 5, a plurality of electrodes 500 are formed on a substrate 560. Each electrode 500 comprises a metal layer 510 and a graphene passivation layer 520 disposed on the top surface of the metal layer 510. An electrically insulating layer 530 encapsulates the electrodes 500 and exposes conductive contacts 540.

The graphene passivation layer may comprise a single monolayer having a thickness of about 0.34 nm, or the graphene passivation layer may comprise more than one monolayer. For example, the graphene passivation layer may comprise 2 or more monolayers. According to at least one embodiment, the graphene passivation layer has a thickness of 3 nm or less, such as, for example, 2 nm or less, 1 nm or less, or 0.7 nm or less.

According to at least one embodiment, the electrode has a maximum cross-sectional dimension (i.e., the largest dimension in the x or y axis based on the orientation shown in FIG. 5) of 10 mm or less. For example, the electrode may have a maximum cross-sectional dimension of 1 mm or less, 500 µm or less, such as, 250 µm or less, 100 µm or less, 50 µm or less, 10 µm or less, or smaller. In at least one embodiment, the electrode can be sized to fit a single cell. For example, a neuron may have a diameter ranging from about 4-100 µm. Therefore, an electrode according to at least one embodiment can be scaled to fit on a single neuron, i.e., the electrode may have a maximum cross-sectional dimension ranging from about 4 to 100 µm. In most embodiments, the passivation layer is substantially thinner than the underlying metal layer. Therefore, the thickness of the electrodes according to the present disclosure are effectively controlled by the size of the metal layer.

In at least one embodiment, the electrode has a conductive contact having a surface area of about 10,000 $\mu m^2$ or less, such as, for example, about 7,500 $\mu m^2$ or less, about 5,000 $\mu m^2$ or less, about 2,500 $\mu m^2$ or less, about 1,000 $\mu m^2$ or less, about 500 $\mu m^2$ or less, about 250 $\mu m^2$ or less, or about 100 $\mu m^2$ or less.

EXAMPLES

Example 1—Forming Electrodes

Figure 7:
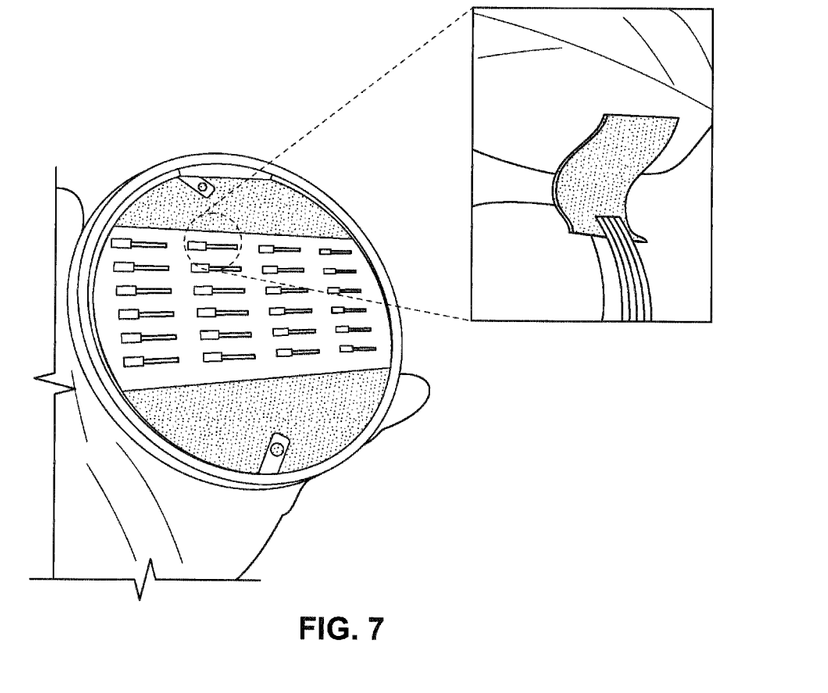
FIG. 7 is a photograph of an array of graphene passivated single electrodes fabricated on a silicon carrier wafer.
Figure 9:
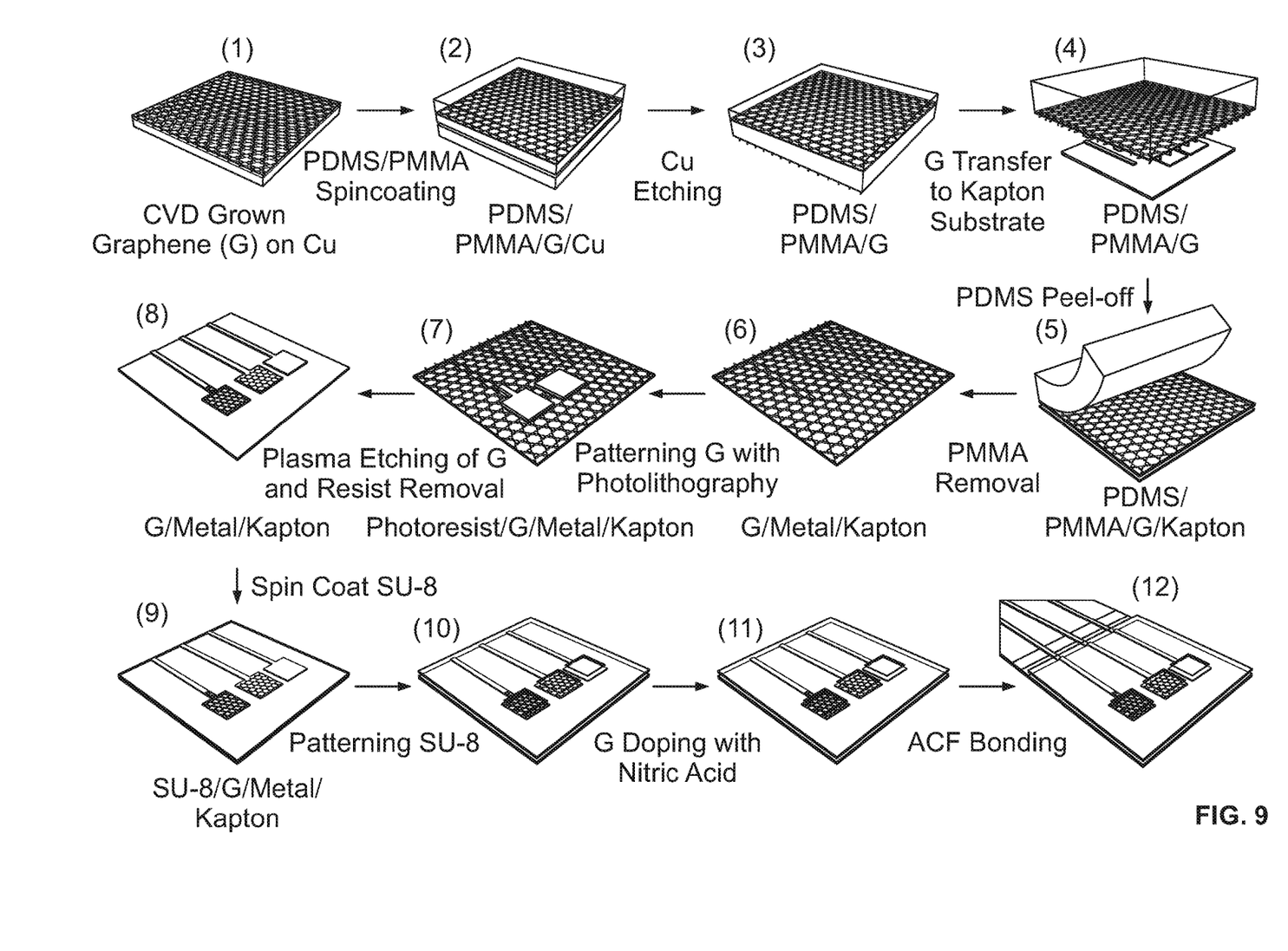
FIG. 9 is a schematic diagram showing a process for making an graphene-passivated electrode array.

An array of neural sensors was made by passivating gold layers with graphene (FIG. 7). A schematic of the process for forming the electrodes is shown in FIG. 9.

In step (1), graphene was grown on a copper foil using chemical vapor deposition (CVD). A transfer layer of poly (methylmethacrylate) (PMMA) backed by poly(dimethylsiloxane) (PDMA) was successively spin-coating the PMMA and PDMA on the graphene-covered copper substrate (step (2)). In step (3), the copper was etched away by selectively etching the copper, leaving the graphene layer attached to the PMMA/PDMA transfer layer.

In step (4), the transfer layer with the graphene layer attached were placed over preformed gold layers formed on a KAPTON® (DuPont) film. The gold layers had been patterned from gold deposited on the KAPTON® film.

The PDMA layer was peeled away from the PMMA layer in step (5), followed by removal of the PMMA layer in an acetone wash (step (6)), leaving the graphene layer covering the gold layers and KAPTON® film.

A photoresist was spin-coated on the graphene layer, followed by patterning and plasma etching of the exposed graphene (step (7)). The photoresist was then removed to reveal the formed electrodes (step (8)). The photoresist was patterned such that some electrodes comprised only gold and other electrodes comprised a graphene layer.

The electrodes were spin-coated with SU-8 photoresist (step (9)) and patterned to review conductive contacts on the electrodes (step (10)).

Selected electrodes were then doped by exposure to nitric acid (step (11)).

An anisotropic conductive film (ACF) was then bound to the formed electrode array for connecting the electrodes to a measuring device.

Example 2—Protective Characteristics

Figure 10:
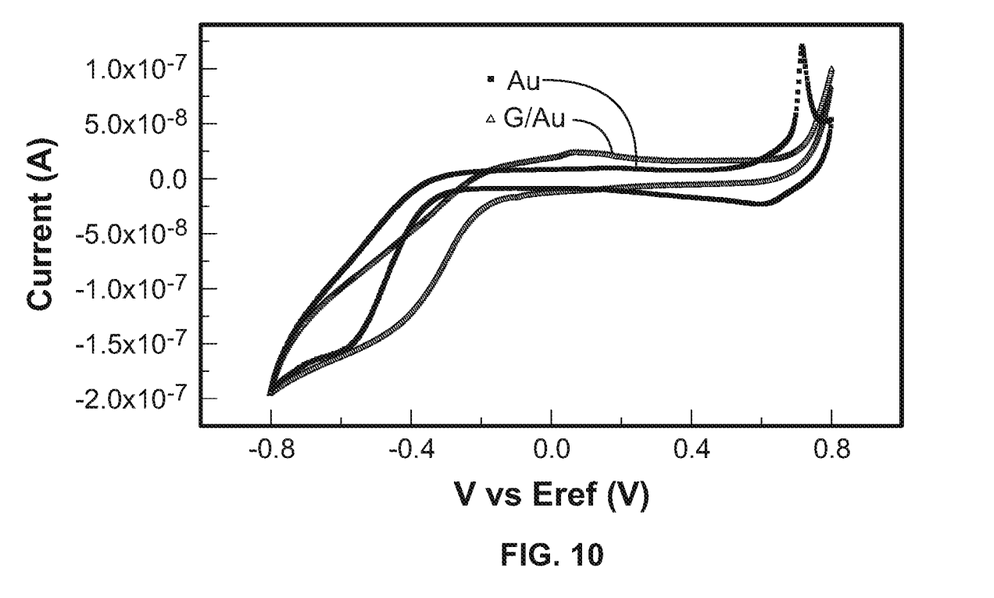
FIG. 10 is a cyclic voltammogram for gold and graphene-coated gold electrodes.

To examine the robustness and corrosion protective characteristics, cyclic voltammetry measurements were carried out on bare gold and graphene/gold electrodes (500×500 µm) in phosphate-buffered saline (PBS) solution. The voltammogram for the bare gold electrode exhibited standard gold oxidation and reduction peaks (FIG. 10), while the graphene-coated gold electrode did not show any faradaic peaks, confirmed that the graphene acted as a protective layer covering the gold surface and inhibiting all electrochemical reactions.

Figure 11:
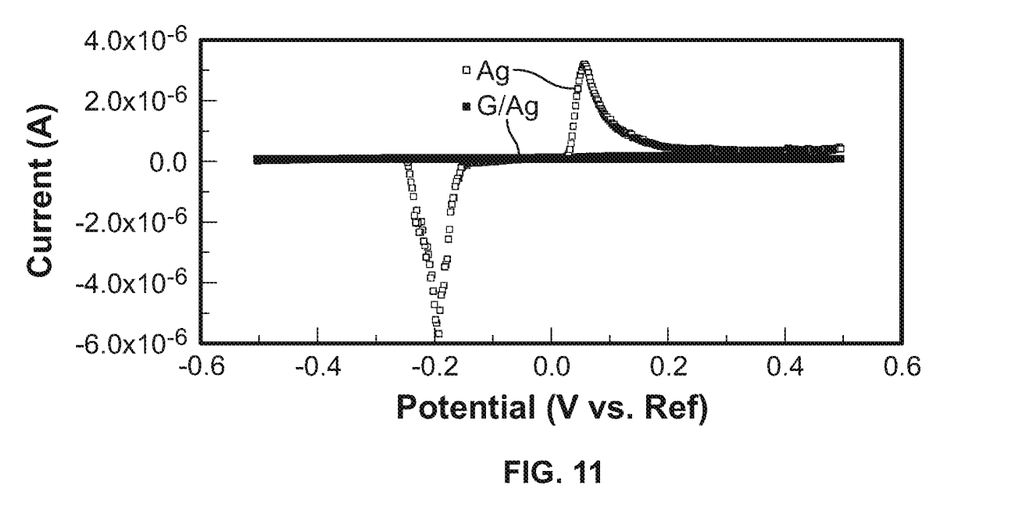
FIG. 11 is a cyclic voltammogram for silver and graphene-coated silver electrodes.
Figure 12:
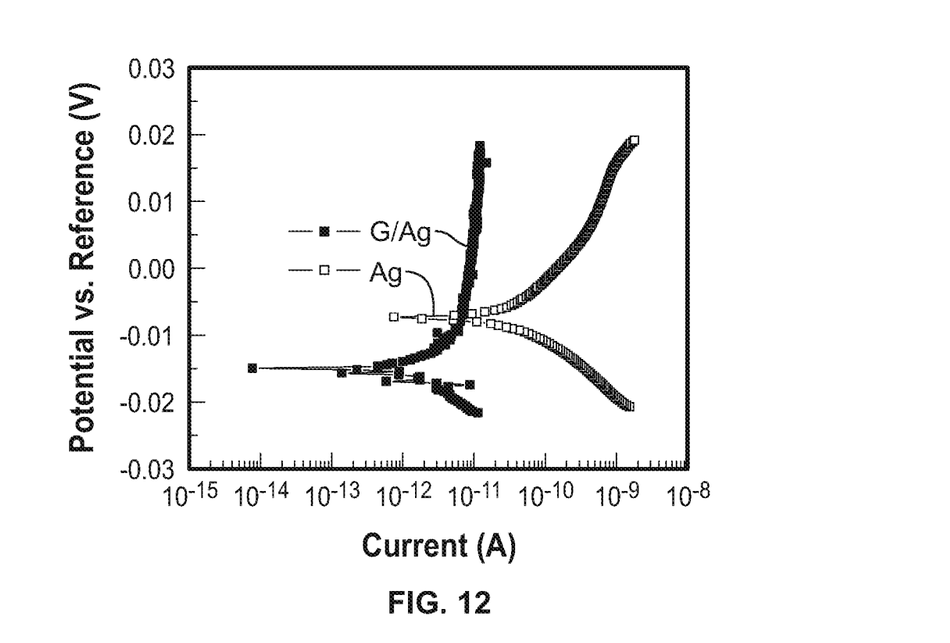
FIG. 12 is a graph of potentiodynamic polarizations tests for silver and graphene-coated silver electrodes.

The cyclic voltammetry tests were repeated with silver and graphene/silver electrodes. Silver is a very corrosive electrode metal, which easily degrades through sulfidation and oxidation when exposed to air. Due to its toxicity and instability, bare silver cannot be used as a neural implant. However, when coated with graphene, all of the electrochemical reactions at the silver surface were eliminated. Cyclic voltammetry and potentiodynamic polarization tests showed that graphene significantly inhibits silver corrosion in PBS (FIGS. 11 and 12).

Figure 13:
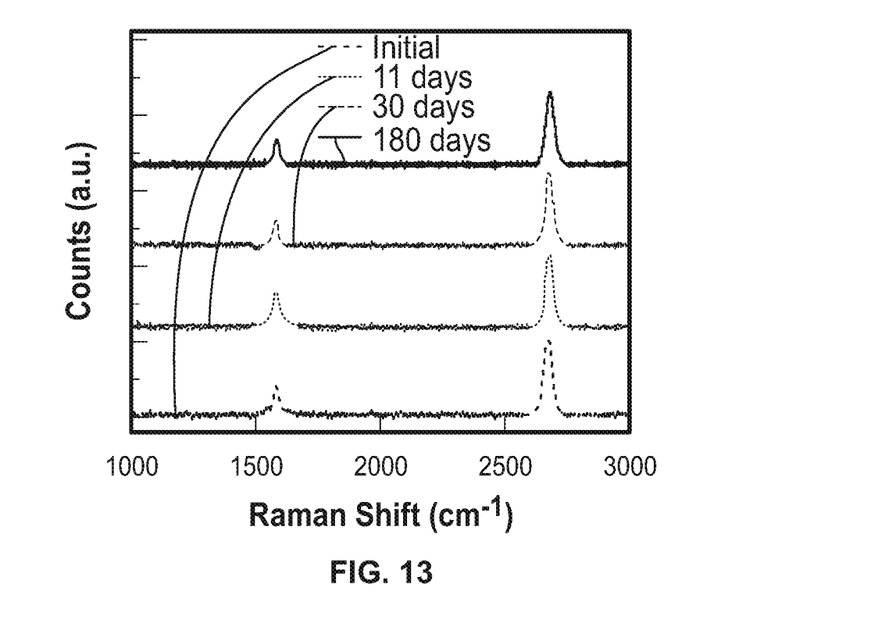
FIG. 13 is a Raman spectrograph of graphene-coated gold electrodes dipped in phosphate-buffered saline solution over time.

To measure the stability of graphene on metal surfaces, Raman spectroscopy was measured on graphene-coated gold electrodes dipped in PBS over an extended period of time (FIG. 13). Clear graphene peaks after 10 days, 30 days, and 180 days show that the graphene was stable and stuck well onto the gold electrode surface and did not delaminate over time.

Example 3—Doped Graphene

Figure 14:
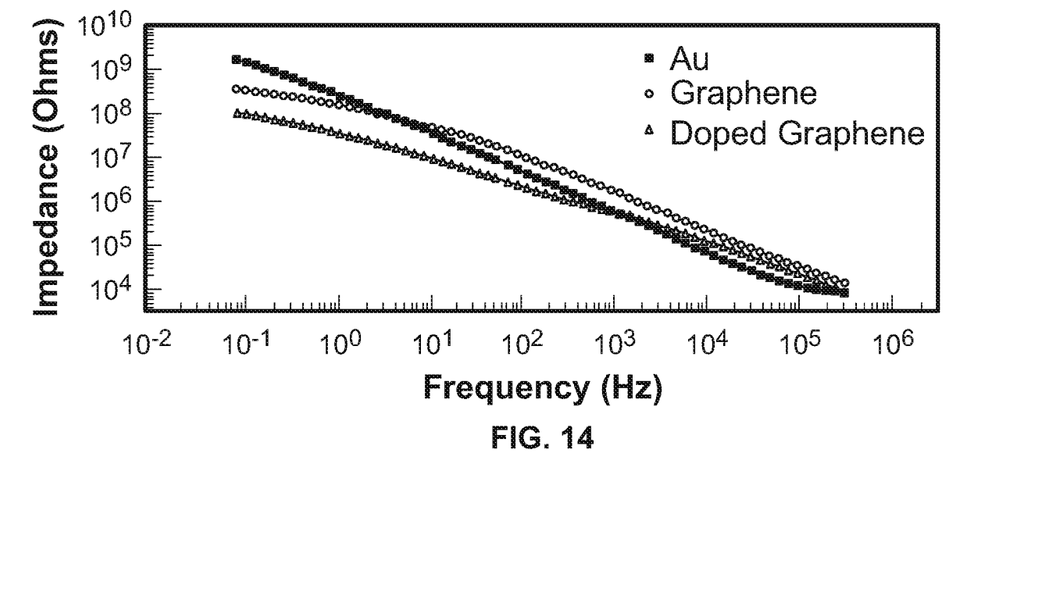
FIG. 14 shows electrochemical impedance spectroscopy (EIS) results for bare gold, graphene, and doped graphene/gold electrodes.

The electrochemical properties of graphene electrodes were characterized by electrochemical impedance spectroscopy (EIS) and cyclic voltammetry. EIS measurements were performed on bare gold, graphene, and doped graphene (2500 µm$^2$). The doped graphene electrodes were doped by dipping the electrode in nitric acid. The EIS results for the gold, graphene, and doped graphene electrodes are shown in FIG. 14. An order of magnitude decrease in the electrode impedance with respect to the bare gold electrode was achieved at low frequencies. Reduction of impedance at low frequencies can have a big impact in suppression of electrical interference noise and electronic noise of the electrode itself.

Figure 15:
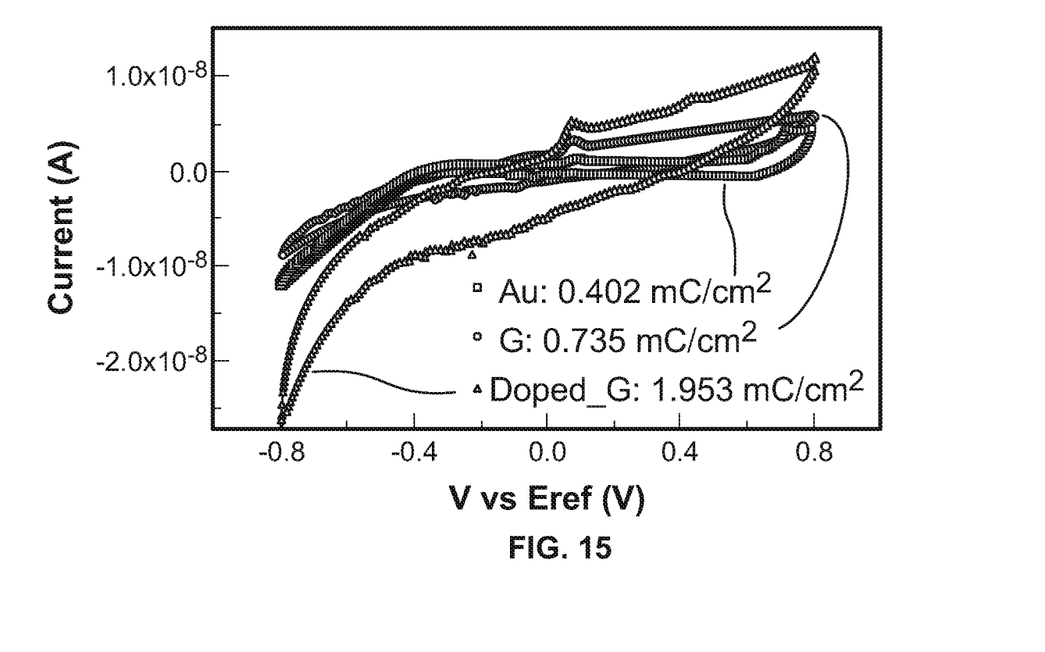
FIG. 15 is a cyclic voltammogram for bare gold, graphene/gold, and doped graphene/gold electrodes.

Cyclic voltammetry measurements (FIG. 15) carried out on the same gold, graphene, and doped graphene show a 5× increase in charge storage capacity for the doped graphene electrode, which could enhance the amount of transferred charge for implantable stimulation electrodes.

Example 4—In Vivo Testing

Lowering the electrode impedance by increasing the effective surface area has been the most standard approach to improve the performance of extracellular microelectrodes. However, it is believed that the ratio between the recorded neural signal and noise level, i.e., the signal to noise ratio (SNR) is a better indicator of electrode performance and scalability.

Figure 8:
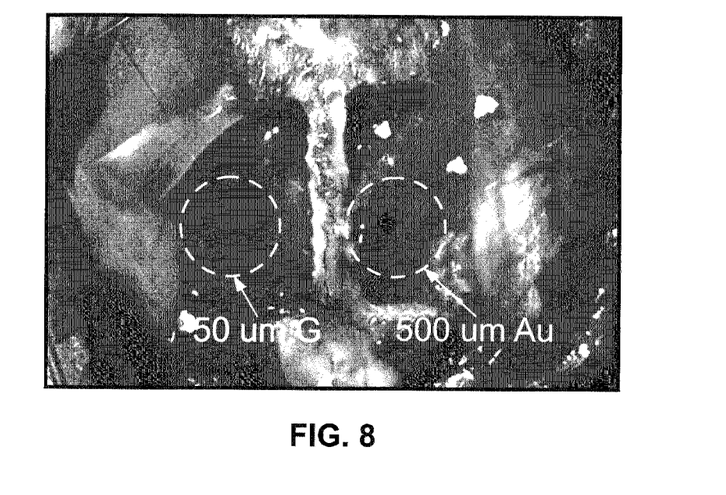
FIG. 8 is a photograph of a graphene-passivated electrode (G) and a gold control electrode placed on the cortical surface of a rat brain.
Figure 16:
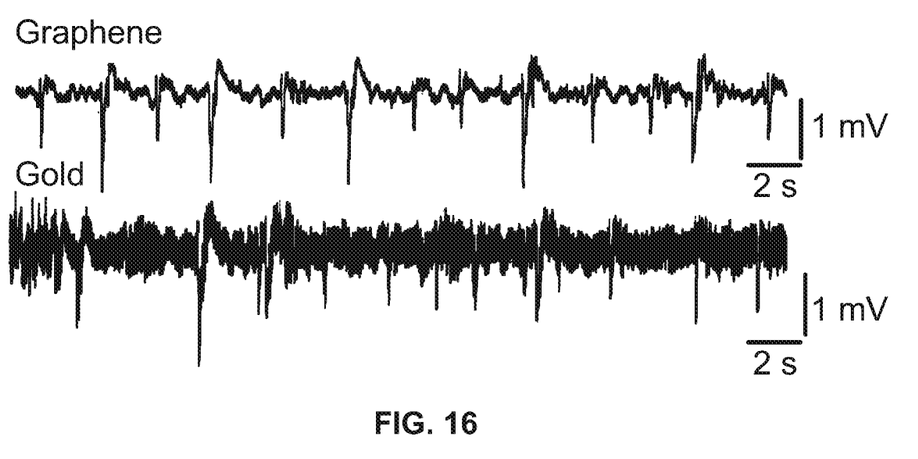
FIG. 16 shows in vivo recordings of doped graphene/gold and bare gold electrodes.

In vivo neural recording experiments were performed on an adult rat animal model to determine the SNR performance of graphene electrodes. An anaesthetized rat was placed with its head fixed in a stereotaxic apparatus. A craniotomy exposed a a 4×8 mm region of cortex in both hemispheres (FIG. 8). To evoke epileptiform activity, crystals of bicuculline methiodide were applied directly to the recording site. Since the aim of the experiment was to investigate the performance of graphene electrodes, single electrodes of various sizes were used instead of electrode arrays. Doped graphene electrodes and gold control electrodes were placed in left and right hemispheres to record simultaneously. Placement of electrodes in either hemisphere was switched in the subsequent recordings to eliminate the possibility of electrode placement related variations. FIG. 16 shows the low-frequency spiking activity recorded by 50×50 µm$^2$ doped graphene and bare gold electrodes. Both electrodes were placed on the same hemisphere and connected to the same amplifier channel in subsequent recordings to ascertain that there are no electrode location or amplifier channel-related variations in the measurements.

Figure 17:
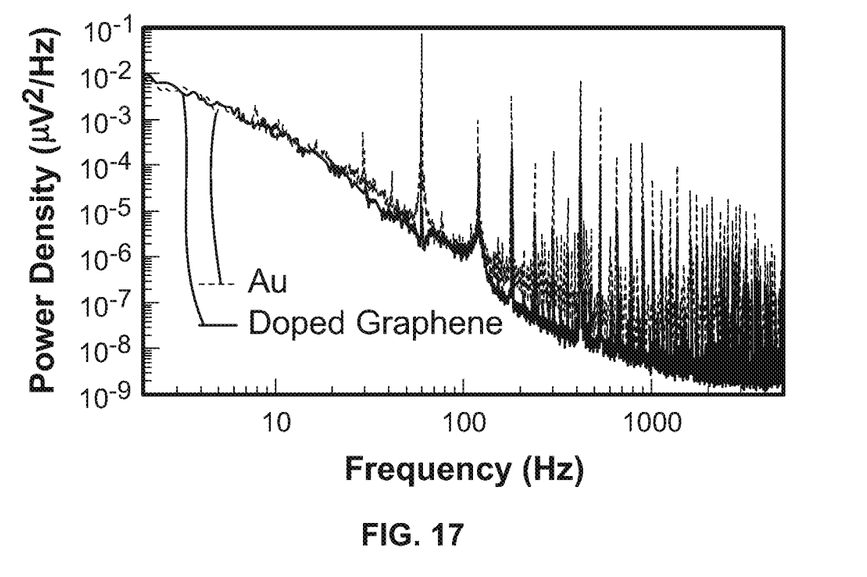
FIG. 17 shows power density spectra of the recordings of FIG. 16.
Figure 18:
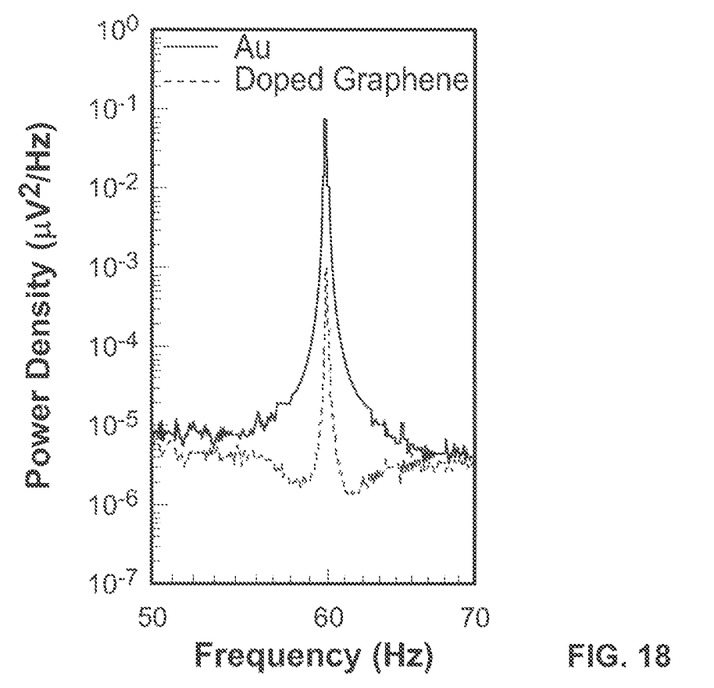
FIG. 18 shows the power density spectra of the recordings of FIG. 16 at 60 Hz.

The SNR (signal amplitude/2×rms noise) of the doped graphene electrode was about 40 dB and the bare gold electrode was about 7 dB. Recordings with doped graphene electrodes were found to have five to six-fold less noise compared to the ones with the gold electrodes of the same size (FIG. 16), although they have comparable impedance values around 1 kHz. Power density spectra of the recordings with doped graphene and bare gold electrodes calculated over 20 s time window is shown in FIG. 17. The doped graphene electrode achieved a significant reduction in 60 Hz electrical interference noise and its harmonics. The power of electrical interference noise was reduced approximately 100 times for the doped graphene electrode (FIG. 18). The suppression of electrical interference noise suggests a clear advantage for studying brain computation in the low local field potential range (LFP: 1-100 Hz), which includes information on slow synaptic potentials. In addition, doped graphene electrodes exhibited lower power in 100 Hz-1000 Hz frequency band, which may indicate that the graphene electrode picks up less biological noise from the activity of the distant sites.

We claim:

1. An electrode for use in the body of a subject, comprising:
   a metal core,
   the metal core defining a proximal surface, a distal surface, and a wall extending so as to connect the proximal surface to the distal surface;
   a continuous graphene passivation layer surmounting the distal surface of the metal core and extending to surmount at least a portion of the wall of the metal core; and
   an electrically insulating material,
   the electrically insulating material being disposed on a portion of the continuous graphene passivation layer such that another portion of the continuous graphene passivation layer is exposed.

2. The electrode of claim 1, wherein the metal core comprises a metal chosen from platinum, gold, iridium, tungsten, stainless steel, silver, copper, nickel, and alloys or combinations thereof.

3. The electrode of claim 1, wherein the electrically insulating material is disposed on the portion of the continuous graphene passivation layer such that the other portion of the continuous graphene passivation layer that surmounts the wall of the metal core is exposed.

4. The electrode of claim 1, wherein the continuous graphene passivation layer is doped such that the continuous graphene passivation layer is p-type graphene.

5. The electrode of claim 1, wherein the continuous graphene passivation layer surmounts essentially the entirety of the distal surface of the metal core and the wall of the metal core.

6. The electrode of claim 1, wherein the electrically insulating material encloses at least a portion of the continuous graphene passivation layer.

7. The electrode of claim 1, wherein the electrically insulating material is arranged such that the other portion of the continuous graphene passivation layer that surmounts the distal surface of the metal core is exposed.

8. The electrode according to claim 1, wherein the continuous graphene passivation layer comprises a single graphene monolayer.

* * * * *